United States Patent
Wilkes

(10) Patent No.: US 9,095,470 B2
(45) Date of Patent: Aug. 4, 2015

(54) LOW-PROFILE REDUCED PRESSURE TREATMENT SYSTEM

(71) Applicant: KCI Licensing, Inc., San Antonio, TX (US)

(72) Inventor: Robert Peyton Wilkes, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 391 days.

(21) Appl. No.: 13/757,445

(22) Filed: Feb. 1, 2013

(65) Prior Publication Data

US 2013/0204214 A1    Aug. 8, 2013

Related U.S. Application Data

(62) Division of application No. 12/006,566, filed on Jan. 3, 2008, now Pat. No. 8,377,017.

(51) Int. Cl.
*A61F 13/00* (2006.01)
*A61F 13/02* (2006.01)
*A61M 1/00* (2006.01)

(52) U.S. Cl.
CPC .......... *A61F 13/0216* (2013.01); *A61M 1/0023* (2013.01); *A61M 1/0088* (2013.01)

(58) Field of Classification Search
CPC .. A61F 13/0216; A61F 1/0023; A61F 1/0088
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

Primary Examiner — Susan Su

(57) ABSTRACT

A low-profile reduced pressure treatment apparatus and system are provided. The apparatus includes a moldable conduit holder, a conduit through the conduit holder, and a flexible base. The conduit holder has first and second bulkhead surfaces, a convex top surface, and a bottom surface adapted to conform to a tissue contact region adjacent to a tissue site. An end of the conduit is substantially flush with the first bulkhead surface and a longitudinal axis of the conduit is substantially perpendicular to the first and second bulkhead surfaces. The base is connected on a first side to the bottom surface of the conduit holder, and extends beyond the first bulkhead surface to form an overlay zone adjacent the first bulkhead surface. An adhesive is disposed on a second side of the flexible base to secure the flexible base to the tissue contact region.

27 Claims, 4 Drawing Sheets

(56) References Cited

U.S. PATENT DOCUMENTS

| | | |
|---|---|---|
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A * | 3/1990 | Moriuchi et al. ............. 604/174 |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0004534 A1 | 1/2005 | Lockwood |
| 2005/0261642 A1* | 11/2005 | Weston ...................... 604/313 |
| 2007/0219512 A1* | 9/2007 | Heaton et al. ............... 604/304 |
| 2007/0233022 A1 | 10/2007 | Henley et al. |
| 2008/0119802 A1* | 5/2008 | Riesinger ..................... 604/313 |
| 2008/0167631 A1* | 7/2008 | Greer .......................... 604/290 |
| 2008/0306456 A1* | 12/2008 | Riesinger ..................... 604/316 |
| 2011/0178481 A1* | 7/2011 | Locke et al. ................. 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0355302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 03/092620 A1 | 11/2003 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

(56) References Cited

OTHER PUBLICATIONS

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đ ukić, Ž. Maksimović, Đ . Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987).
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92.
V.A. Solovev, Dissertation Abstract, Treatment and Prevention of Suture Failures after Gastric Resection (S.M. Kirov Gorky State Medical Institute, Gorky, U.S.S.R. 1988).
V.A.C.® Therapy Clinical Guidelines: A Reference Source for Clinicians (Jul. 2007).

* cited by examiner

LOW-PROFILE REDUCED PRESSURE TREATMENT SYSTEM

CROSS REFERENCE TO RELATED APPLICATIONS

This Application is a Divisional of U.S. patent application Ser. No. 12/006,566 filed on Jan. 3, 2008, now U.S. Pat. No. 8,377,017 B2 issued Feb. 19, 2013, the contents of which are hereby incorporated by reference in their entirety.

BACKGROUND OF THE INVENTION

1. Field of the Invention

The present invention relates generally to tissue treatment systems and in particular to low-profile reduced pressure treatment systems.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. The porous pad contains cells or pores that are capable of distributing reduced pressure to the tissue and channeling fluids that are drawn from the tissue. The porous pad often is incorporated into a dressing having other components that facilitate treatment.

Traditionally, dressings have been rather cumbersome and difficult to apply to small wounds. Simply sitting on or rolling onto a dressing may cause significant patient discomfort, or pressure-induced injury, particularly at contact with relatively stiff components such as tubing connections, elbows, and other components. Moreover, these actions may compress the dressing and interfere with the application of reduced pressure. Furthermore, the profile of these dressings and any protuberances present the likelihood of snagging on patient clothing or surroundings during normal activity, a risk associated with pain and possible re-injury of tissue.

Accordingly, there is much demand for improved dressings that alleviate the disadvantages of known dressings.

All references cited herein are incorporated by reference to the maximum extent allowable by law. To the extent a reference may not be fully incorporated herein, it is incorporated by reference for background purposes and indicative of the knowledge of one of ordinary skill in the art.

BRIEF SUMMARY OF THE INVENTION

The problems presented in known reduced pressure treatment systems are solved by the systems and methods of the present invention. A low-profile reduced pressure treatment apparatus and system are provided in accordance with the principles of the present invention.

The principles of the present invention further provide for a centralized RCP data repository that may be used by check cashing companies and other organizations to identify checks that have been cashed via an RCP transaction prior to a traditional check clearing process as performed by the banking system. The centralized RCP data repository may be queried by the RCP transaction process or manually to prevent more than one presentation of a check to the banking system.

An embodiment of the low-profile reduced pressure treatment system includes a moldable conduit holder, a conduit received by the conduit holder, a base, a porous pad, a drape, and a reduced pressure source fluidly connected to the conduit to deliver reduced pressure through the conduit and the porous pad. The conduit holder has substantially parallel first and second bulkhead surfaces, a convex top surface, and a bottom surface adapted to substantially conform in shape to a tissue contact region adjacent to a tissue site. The conduit is received by, the conduit holder such that an end of the conduit is substantially flush with the first bulkhead surface and a longitudinal axis of the conduit is substantially perpendicular to the first and second bulkhead surfaces. The base has a first side connected to the bottom surface of the conduit holder, the base extending beyond the first bulkhead surface to form an overlay zone adjacent the first bulkhead surface. An adhesive is disposed on a second side of the base to secure the base to the tissue contact region adjacent to the tissue site. The porous pad includes a primary delivery region configured to contact the tissue site and a bridge region configured to contact the overlay zone of the base and apply a flexible transition to the tissue site. The drape is sized to cover and create a sealed space around the conduit holder and the porous pad.

Also in accordance with the principles of the present invention, a process for making and using a low-profile reduced pressure treatment apparatus and system is provided. One embodiment for making a low-profile reduced pressure treatment apparatus includes positioning a first flexible membrane on an arcuate form, positioning a conduit on the first flexible membrane, extruding silicone onto and around the conduit, positioning a second flexible membrane over the silicone and the conduit, securing edges of the second flexible membrane to edges of the first flexible membrane, and securing the first flexible membrane to a drape having dimensions greater than the first flexible membrane so that the drape extends beyond the edges of the first flexible membrane adjacent to an aperture of the conduit.

One process for using a low-profile reduced pressure treatment apparatus includes positioning a first flexible membrane so that an overlay zone is adjacent to the tissue site and a conduit holder is adjacent to the overlay zone opposite the tissue site; positioning a porous pad so that a bridge region is aligned with the overlay zone and a primary delivery region is aligned with the tissue site; connecting the porous pad to a reduced pressure source through a conduit in the conduit holder; positioning a second flexible membrane over the conduit holder and the porous pad; sealing the second flexible membrane to the tissue contact region; and applying reduced pressure from the reduced pressure source to the tissue site through the conduit and the porous pad.

Other objects, features, and advantages of the present invention will become apparent with reference to the drawings and detailed description that follow.

DETAILED DESCRIPTION OF THE PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

In the context of this specification, the term "reduced pressure" generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

Figure 1:
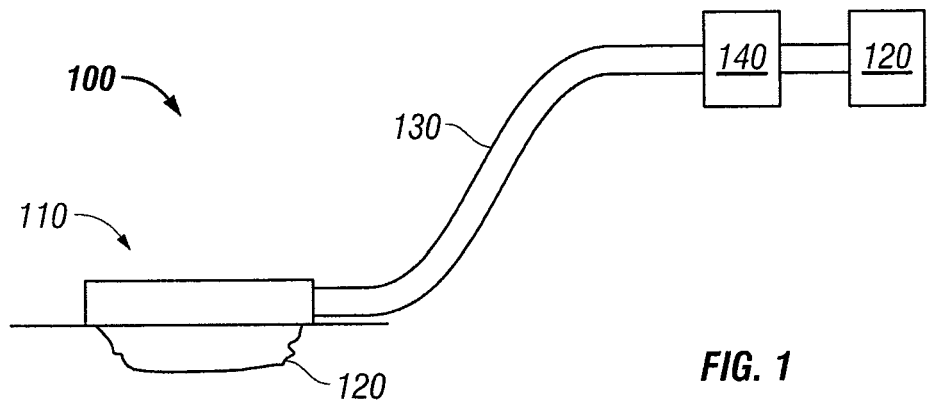
FIG. 1 illustrates a schematic view of a reduced pressure treatment system according to the present invention.

FIG. 1 is a schematic diagram of a reduced pressure treatment system 100 incorporating the novel features of the invention. The reduced pressure treatment system 100 comprises a dressing 110, which is applied to a tissue site 120 for treatment. Dressing 110 is fluidly connected to a reduced pressure source 120 by a conduit 130. In certain embodiments, the reduced pressure system 110 may also include a canister 140 for collecting liquid and other non-gaseous exudates extracted from a tissue site.

Figure 2:
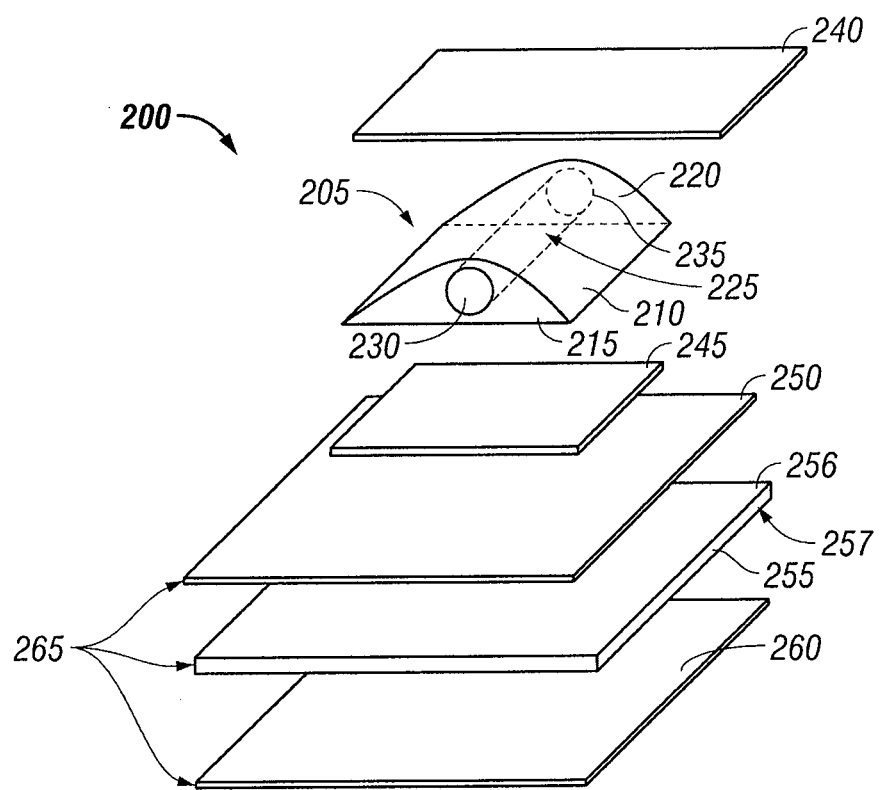
FIG. 2 illustrates an exploded view of a low-profile adapter according to the present invention.

FIG. 2 is an exploded view of an embodiment of a low-profile adapter 200. In this embodiment, the adapter 200 comprises a conduit holder 205, a first bulkhead surface 215, and a second bulkhead surface 220 that is substantially parallel to the first bulkhead surface 215. In this embodiment, the conduit holder 205 has a convex top surface 210 to minimize the profile of the conduit holder 205. The conduit holder 205 also includes a conduit 225 that extends through the length of the conduit holder 205, having an aperture 230 on the first bulkhead surface 215 and an aperture 235 on the second bulkhead surface 220.

The conduit holder 205 is constructed from any material that may be extruded or injected into a mold, such as room temperature vulcanizing (RTV) silicone. The conduit 130 may be inserted into or connected to the conduit 225 to establish a fluid path between the aperture 230 and the reduced pressure source 120.

Depending on the composition of the conduit holder 205, the conduit holder 205 may optionally be enclosed between flexible membranes of a material more suitable for tissue contact, such as a nitrile film, as illustrated by the flexible membranes 240 and 245. In such an embodiment, the flexible membrane 245 is attached to the flexible membrane 250.

Alternatively, the flexible membrane 245 may be omitted and the flexible membrane 240 may be attached directly to the flexible membrane 250. The flexible membrane 250 is preferably a polyurethane material. A drape 255 having adhesive surface 256 is bonded to the flexible membrane 250 on one side. The drape 255 may include an optional biocompatible adhesive surface 257 on the side opposite the adhesive surface 256. The biocompatible adhesive surface 257 may consist of any suitable bonding agent, such as an acrylic adhesive or hydrogel. The biocompatible adhesive surface 257 may be applied to intact tissue to secure the low-profile adapter in position when applied to a tissue site. If the drape 255 includes the biocompatible adhesive surface 257, a protective liner 260 is applied to the biocompatible adhesive surface 257 to preserve the adhesive and facilitate handling. The protective liner 260 is removed to expose the underlying adhesive before application to the tissue site 120. The flexible membrane 250, the drape 255, and optionally, the protective liner 260 comprise a base 265. The drape 255 generally is constructed from any flexible material having a sufficiently high moisture vapor transmission rate (MTVR) to preclude tissue maceration, typically greater than 600 mg/m$^2$/day. Polyurethane is an example of a suitable material for the drape 255. Because of the flexibility of the flexible membrane 250 and the drape 255, the base 265 readily conforms to the contours of most tissue sites.

Figure 3:
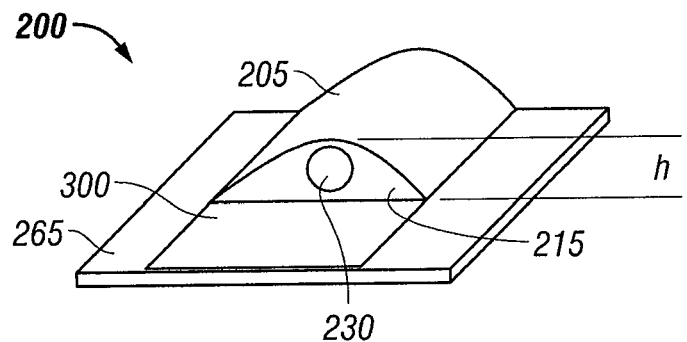
FIG. 3 illustrates a perspective view of the assembled low-profile adapter of FIG. 2 according to the present invention.

FIG. 3 is a perspective view of the assembled low-profile adapter 200. The conduit holder 205 has a height h, as measured between the apex of the first bulkhead surface 215 and the base 265. As FIG. 3 illustrates, the base 265 extends beyond the first bulkhead surface 215 to form a bridge overlay zone 300 adjacent to the first bulkhead surface 215 and the aperture 230.

Figure 4:
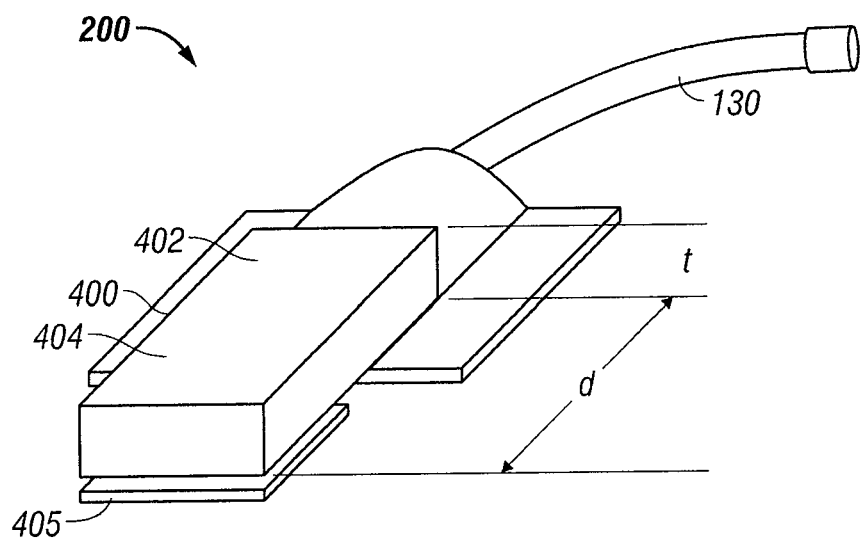
FIG. 4 illustrates a perspective view of the assembled low-profile adapter of FIG. 3 with a porous pad in position over a bridge overlay zone according to the present invention.

FIG. 4 is a perspective view of the assembled low-profile adapter 200 with a porous pad 400 in position over the bridge overlay zone 300 (not visible in FIG. 4). The porous pad 400 generally includes a porous bridge 402 and a primary delivery region 404. FIG. 4 also illustrates a section of the conduit 130, which is connected on one end to the aperture 235 (not shown in FIG. 4). The porous pad 400 has a thickness, t, sufficient to cover the aperture 230 in the first bulkhead surface 215, which is typically the same dimension as the height h of the conduit holder 205. The porous pad 400 also has a depth d sufficient to extend from the first bulkhead surface 215 and overhang the bridge overlay zone 300 to cover a tissue site. FIG. 4 also illustrates an optional porous extension 405, which may be inserted into a tissue site for deeper penetration. Although the porous extension 405 is depicted in FIG. 4 as a separate component, the porous extension 405 may be an integral component of the porous pad 400 so that the porous pad 400 and the porous extension 405 form a single component. Likewise, the porous pad 400 and the porous extension 405 are illustrated as simple block pieces, but they may be adapted to any desired shape. For example, the porous pad 400 may be cut to conform to the profile of the conduit holder 205 or to the shape of an irregular tissue site.

The porous pad 400 and the porous extension 405 represent any material known in the art to be suitable for reduced pressure treatment, the size and shape of which may be varied to accommodate tissue sites of various size and shape. Preferably, the porous pad 400 and the porous extension 405 include a plurality of flow channels or pathways to facilitate the distribution of reduced pressure or fluids to or from the tissue site. In one embodiment, the porous pad 400 and the porous extension 405 are porous foam that includes interconnected cells or pores that act as flow channels and a pressure manifold. The porous foam may be polyurethane or any other type of open-cell, reticulated foam, such as GRANUFOAM manufactured by Kinetic Concepts, Inc. of San Antonio, Tex. If open-cell foam is used, the porosity may vary, but is preferably about 400 to 600 microns. Alternatively, gauze or any other material suited to a particular biological application may be used to construct the porous pad 400 and the porous extension 405.

Figure 5:
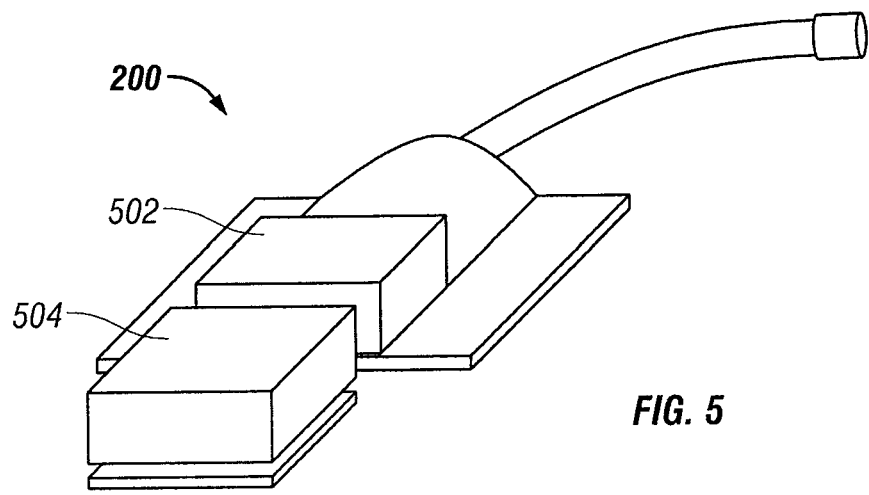
FIG. 5 illustrates a perspective view of the assembled low-profile adapter of FIG. 3 with an alternate embodiment of the porous pad according to the present invention.

FIG. 5 is a perspective view of the low-profile adapter 200 with an alternative embodiment of a porous pad. As FIG. 5 illustrates, a porous pad may be comprised of one or more discrete components, such as a porous bridge 502 and a primary delivery component 504. Such an alternative embodiment may be advantageous for packaging a universal bridge component with the low-profile adapter 200, while permitting additional components to be fit to a particular tissue site as needed.

Figure 6:
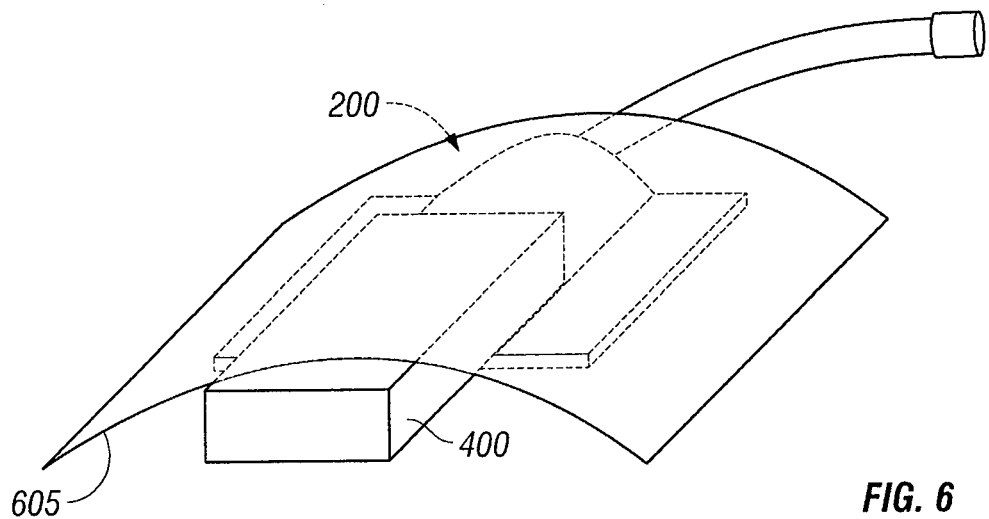
FIG. 6 illustrates a perspective view of the assembled low-profile adapter and porous pad of FIG. 4 covered by a drape according to the present invention.

FIG. 6 is a perspective view of the low-profile adapter 200, a porous pad 400, and a drape 600. The drape 600 covers the low-profile adapter 200 and the porous pad 400, and includes an adhesive on the surface 605 that is applied to a tissue contact region adjacent to a subject tissue site (not shown). The adhesive may consist of any suitable bonding agent, such as an acrylic adhesive or hydrogel. The seal isolates the tissue site from the surrounding environment and assists in maintaining a reduced pressure at the tissue site when reduced pressure is applied. The convex top surface 210 provide tapered lateral edges, which minimize the risk of leaks between the drape 600 and the tissue contact region adjacent to the tissue site. The adhesive may also secure the low-profile adapter 200 and the porous pad 400 in position if the drape 255 does not include the optional biocompatible adhesive surface 257. Like the drape 255, the drape 600 generally is constructed from any flexible material having a sufficiently high moisture vapor transmission rate (MTVR) to preclude tissue maceration, typically greater than 600 mg/m$^2$/day.

In operation, the protective liner 260 (if present) is removed to expose the adhesive surface 257 (if present), and the low-profile adapter 200 is positioned so that the bridge overlay zone 300 is over intact tissue and immediately adjacent to a tissue site 120. A porous pad (such as porous pad 400) is positioned so that it extends from the first bulkhead surface 215 and overhangs the bridge overlay zone 300 to cover the tissue site 120, while one end covers the aperture 230 in the first bulkhead surface 215. The drape 600 is then placed over the low-profile adapter 200 and the porous pad 400, and the edges of the drape 600 are pressed against intact tissue surrounding the low-profile adapter 200 and the intact tissue surrounding the tissue site 120. The conduit 130 is then connected on one end to the conduit 225 through the aperture 235 in the second bulkhead surface 220, and on the other end to the collection canister 140 or the reduced pressure source 125. Reduced pressure may then be delivered to the tissue site 120 through the conduit 130, the conduit 225, and the pad 400.

Figure 7:
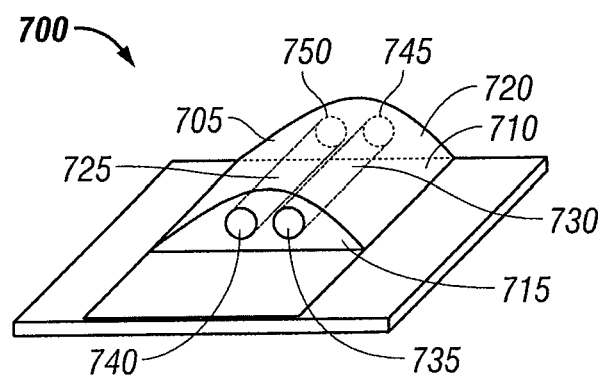
FIG. 7 illustrates a perspective view of an alternate embodiment of a low-profile adapter having multiple conduits according to the present invention.

FIG. 7 is a perspective view of an alternate embodiment of a low-profile adapter 700. In this embodiment, the adapter 700 comprises a conduit holder 705 having a convex top surface 710, a first bulkhead surface 715, and a second bulkhead surface 720 that is substantially parallel to the first bulkhead surface 715. The conduit holder 705 also includes two conduits 725 and 730 that extend through the length of the conduit holder 705, having two apertures 735 and 740 on the first bulkhead surface 715, and two apertures 745 and 750 on the second bulkhead surface 720. Multiple conduits, such as those depicted in FIG. 7, may be advantageous for applications such as pressure monitoring and fluid distribution in conjunction with reduced pressure application. Alternatively, a multi-lumen conduit may be substituted for any pair of conduits.

Figure 8:
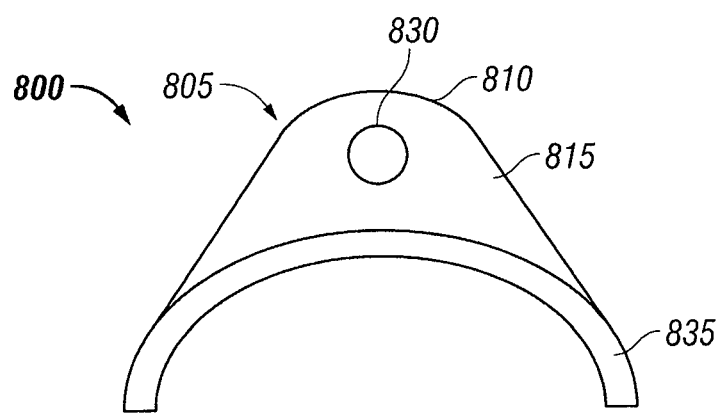
FIG. 8 illustrates a front view of an alternate embodiment of a low-profile adapter having a concave molded base according to the present invention.

FIG. 8 is a front view of another alternate embodiment of a low-profile adapter 800. In this embodiment, the low-profile adapter 800 comprises a conduit holder 805 having a convex top surface 810, a first bulkhead surface 815, and a second bulkhead surface (not shown) that is substantially parallel to the first bulkhead surface 815. The conduit holder 805 also includes a conduit (not shown) that extends through the length of the conduit holder 805, having an aperture 830 on the first bulkhead surface 815 and an aperture (not shown) on the second bulkhead surface (not shown). The conduit holder 805 is attached to a base 835 that is molded to conform to the contours of a particular tissue site, such as on a finger or other limb. The base 835 in such an embodiment may be constructed from any material that may be extruded or injected into a mold, such as room temperature vulcanizing (RTV) silicone, or from any biocompatible material that is readily manipulated at room temperature.

A low-profile adapter embodying the principles and features described above may generally be constructed as follows, referring to the embodiment described above as the low-profile adapter 200 having the flexible membranes 240 and 245 for illustration. First, the flexible membranes 240 and 245 are cut into substantially equal shapes and sizes, and the flexible membrane 245 is anchored or placed onto a form of desired contour or shape. For the low-profile adapter 200, the form should be substantially flat, but the form may have a convex surface to form alternate embodiments such as the low-profile adapter 800. The conduit 225 is then positioned across the flexible membrane 245. The material of the conduit holder 205 is then extruded onto and around the conduit 225, forming the first bulkhead surface 215 and the second bulkhead surface 220 around each end of the conduit 225 so that the aperture 230 is substantially flush with the first bulkhead surface 215 and the aperture 235 is substantially flush with the second bulkhead surface 220. The material should be shaped to form the convex top surface 210. The flexible membrane 240 is then stretched across the conduit 225 and the surrounding material, and the edges of the flexible membrane 240 are secured to the edges of the flexible membrane 245 using any adhesive, bonding agent, thread, staples, or other suitable means. The drape 255 is prepared by sizing it so that a border of desired width extends laterally and in front of the conduit holder 205. For small tissue sites, the border width may be on the order of 1 cm. Allowing time for the material surrounding the conduit 225 to cure, if necessary, the flexible membrane 245 is placed on the adhesive surface 256 of the drape 255. The flexible membrane 250 is placed around the conduit holder 225 to cover any exposed adhesive on the adhesive surface 256. Finally, the protective liner is applied to the adhesive surface 257, if desired.

One skilled in the art will see that the present invention can be applied in many areas where there is a need to provide tissue treatment. For example, the shape of the low-profile adapter may be changed to accommodate anatomical features, as well as flat, convex, or saddle-shaped skin contours. Likewise, the shape and dimensions of the porous bridge may be altered to accommodate various sizes and shapes of tissue sites. Additionally, multiple low-profile adapters may be used in series using small conduits and interconnecting ports, which may be advantageous for hardware penetration points of orthopedic external fixation.

It should be apparent from the foregoing that an invention having significant advantages has been provided. While the invention is shown in only a few of its forms, it is not so limited and is susceptible to various changes and modifications without departing from the spirit thereof.

What is claimed:

1. A reduced pressure treatment apparatus comprising:
   a conduit holder having a first bulkhead surface, a second bulkhead surface, a top surface being convex in shape, and a bottom surface conformable in shape to a tissue contact region proximate to a tissue site;
   a first conduit extending through the conduit holder from the first bulkhead surface to the second bulkhead surface and adapted to receive reduced pressure from a source of reduced pressure;
   a flexible membrane connected to the bottom surface of the conduit holder and extending beyond the first bulkhead surface to form a bridge overlay zone adjacent the first bulkhead surface; and
   a porous pad having a primary delivery region configurable to contact the tissue site and a porous bridge configurable to contact the first bulkhead surface in fluid communication with the first conduit and the bridge overlay zone.

2. The apparatus of claim 1, further comprising a second conduit having a first end in fluid communication with the first conduit at the second bulkhead surface and adapted for receiving reduced pressure from the source of reduced pressure.

3. The apparatus of claim 2, wherein the first end of the second conduit extends into the first conduit.

4. The apparatus of claim 3, wherein the first end of the second conduit is flush with the first of bulkhead surface.

5. The apparatus of claim 2, wherein the second conduit has a longitudinal access perpendicular to the second bulkhead surface.

6. The apparatus of claim 2, further comprising a drape configurable to cover and create a sealed space around the first conduit, the first end of the second conduit, the conduit holder, and the porous pad, wherein the first conduit is parallel to the tissue contact region.

7. The apparatus of claim 1, wherein the conduit holder is formed from room-temperature-vulcanizing silicone.

8. The apparatus of claim 1, wherein the flexible membrane is a polyurethane material.

9. The apparatus of claim 1, wherein the flexible membrane is adhesively connected to the bottom surface of the conduit holder.

10. The apparatus of claim 1, further comprising a drape having a first side adhesively connected to the flexible membrane.

11. The apparatus of claim 10, wherein the drape has a second side having an adhesive surface adapted to be applied to the tissue contact region.

12. The apparatus of claim 11, wherein the adhesive surface is biocompatible.

13. The apparatus of claim 12, wherein the adhesive surface is an acrylic material.

14. The apparatus of claim 11, further comprising a protective liner covering the adhesive surface.

15. The apparatus of claim 1, wherein the conduit holder further comprises:
    a first flexible membrane forming the bottom surface;
    a second flexible membrane forming the top surface; and
    a moldable material disposed between the first and second flexible membranes to encase the first conduit between the first and second flexible membranes.

16. The apparatus of claim 15, wherein the first and second membranes are nitrile film.

17. The apparatus of claim 1, further comprising a porous extension region configurable to extend perpendicularly from the primary delivery region into the tissue site.

18. The apparatus of claim 17, wherein the porous tension region and the primary delivery region include a plurality of flow channels to facilitate distribution of reduced pressure and fluids from the tissue site.

19. The apparatus of claim 17, wherein the porous extension region and the primary delivery region are a single component.

20. The apparatus of claim 1, wherein the porous bridge region has a side surface contacting the first bulkhead surface and having a cross-sectional shape similar to the first bulkhead surface.

21. The apparatus of claim 1, wherein the porous pad has a thickness (t) and the conduit holder has a height (h) that are substantially equal.

22. The apparatus of claim 1, wherein the porous bridge region has a side surface contacting the first bulkhead surface and being substantially perpendicular to the tissue site.

23. The apparatus of claim 1, wherein the primary delivery region and the porous bridge region are separate components, each having a contact surface in fluid communication with the contact surface of the other.

24. The apparatus of claim 1, wherein the primary delivery region and the porous bridge region are discrete components.

25. The apparatus of claim 1, wherein the porous pad comprises open-cell foam.

26. The apparatus of claim 25, wherein the porous pad is polyurethane.

27. The apparatus of claim 25, wherein the open cells of the porous pad are interconnected to act as flow channels to facilitate the distribution of reduced pressure from the tissue site.

* * * * *